Sept. 18, 1956 R. BAERMAN ET AL Plant Pat. [illegible]
GLADIOLUS PLANT
Filed Aug. 18, 1955
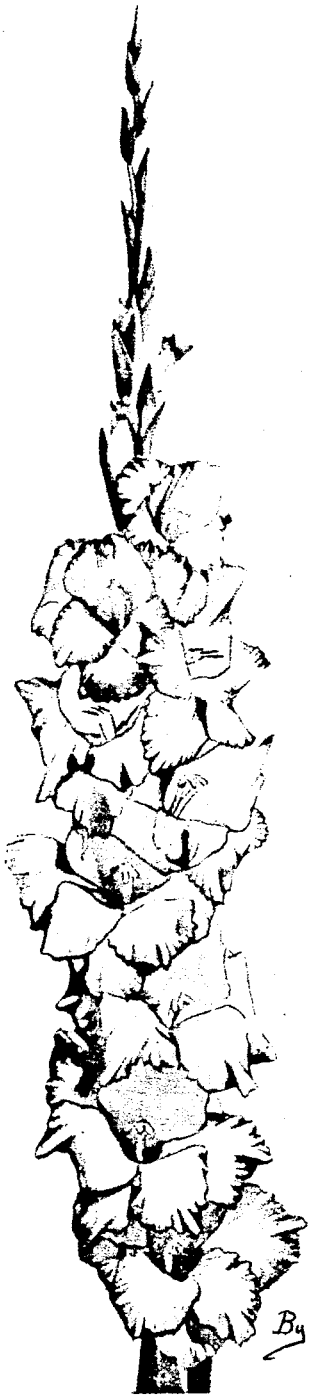
INVENTORS
RALPH BAERMAN and
CARL H. FISCHER.
By Lamont Johnston
ATTORNEY United States Patent Office Plant Pat. 1,517
Patented Sept. 18, 1956

1,517

GLADIOLUS PLANT

Ralph Baerman, Arlington, Va., and Carl H. Fischer, St. Charles, Minn., assignors to Selected Glads, Inc., Nashville, Tenn., a corporation of Tennessee Application August 18, 1955, Serial No. 529,372

1 Claim. (Cl. 47—60)

Our present invention relates to a new and improved variety of gladiolus plant, and is notable for the size and quantity of bloom, delicate and distinctive coloring, heavy substance of petals, and apparent freedom from disease.

This new variety is the result of a cross between the varieties Beauty's Bush (unpatented) as the seed parent, and Rose Charm (unpatented) as the pollen parent. It was produced by hand pollenation done by the first-named inventor in a rented garden near his home when living at Suitland, Maryland, and it exhibits the traits of both parents. It was asexually reproduced in Minnesota by the second-named inventor by natural increase from cormels. Through several generations its characteristics have proved to be permanently fixed.

The illustration forming a part of this application shows a spike of the bloom of this new variety in approximately its true natural coloring.

In the following detailed description, color plate references are to Ridgway's Color Standards and Nomenclature, edition of 1912. Where there are other references to color, the ordinary dictionary meaning of the term is intended.

THE PLANT

Growth: Very vigorous, averaging 62 inches in height when grown with an adequate moisture supply. It is a very rapid propagator and an easy germinator, although the bulblets are small.

Blooming habit: Each spike will have 7 to 10 florets open at one time outdoors and florets will not wilt even in 100-degree weather. The variety is an early bloomer, flowering from mature No. 1 bulbs in 65 to 70 days, depending upon the reason.

Disease resistance: Very resistant to diseases, such as Fusarium wilt, Sclerotinia dry rot, and Botrytis, to which gladiolus varieties are subject, even when grown alongside another variety which is disease-infested.

Stems: Straight, stiff, and wiry; Parrot Green in color (Plate VI); diameter at base averages nearly an inch.

Foliage: Spinach Green (Plate V); averages 2½ inches wide and 36 inches high.

Corms: Well-formed, with a moderately high crown and heavy, slightly corrugated husks. Corms from adult plants average 3 inches in diameter.

THE FLOWER

Spike: Long and slender, bearing 18 to 24 buds and flowers, 3 to 5 of which open the first day, following which 7 to 10 are open at one time until all the buds have opened.

Bud:

*Size.*—Opening buds average 3 inches in length.

*Color.*—Deep Rose Pink (Plate XII), being a slightly warmer pink than the edges of the open flower.

*Opening.*—Seven to 10 florets open at one time with six to eight additional buds showing color at the same time.

Flower:

*Arrangement.*—Flowers are regularly spaced on the spike except that the first two or three are often farther apart than succeeding ones. All florets face in the same direction with great consistency.

*Size.*—Lower blooms average 5 inches across when permitted to bloom on the plant in the field. Florets maintain their size well but progressively diminish a little in diameter as they bloom up the spike. When cut in bud and opened indoors, florets average 4½ inches in diameter.

*Form.*—Wide-open, round, regular, and gently recurved; six petals, with one or two throat petals smaller than the others.

*Keeping qualities.*—Flowers keep and ship exceptionally well.

Petals:

*Shape.*—Petals are unusually wide, being nearly round except for an extension at the tip caused by a slightly raised midrib. There is a slight but not marked tendency to waving or corrugation at the edges of the petals.

*Size.*—Petals are 2 to 2½ inches wide, except for one or two throat petals which are 1½ to 1¾ inches wide.

*Aspect.*—Substance is about 1/16 of an inch thick, contradictory to the extreme delicacy of the coloring. Smooth and waxy in texture, with a glossy, frosty sheen.

*Fragrance.*—None.

*Color.*—The foundation hue is milk-white overlaid at the extreme outer edge by a corona or halo of a tint halfway between Amaranth Pink (Plate XII) and Deep Rose Pink (Plate XII). This corona is more pronounced at the tips of the larger (and longer) petals. The deepest portion of the corona or picoteeing is never more than ¼ inch wide and quickly blends into a much lighter tint which lies halfway between Pale Amaranth Pink (Pl. XII) and Rose Pink (Pl. XII), then to a tint so pale it disappears into the white. The total tinted outer portion of the petal is ¼ to ⅝ of an inch wide, the prevailing effect being of a white flower with a cool rose-pink edging. The throat petals have a faint suffusion of cream beginning about ¾ of an inch from the outer tips of the petals. Deeper in the throat this cream becomes pale Sulphur Yellow (Pl. V) and finally, in the deepest portion of the throat, a very pale Viridine Yellow (Pl. V).

Reproductive organs:

*Stamens.*—Of average size; white, with open side of anthers edged with pale Amparo Purple (Pl. XI). Occasional spikes may not produce pollen, in which case the anthers remain white.

*Pistils.*—White; three-pronged, extending well beyond the stamens.

COMPARISONS

The known varieties which our new variety most resembles are Corona (unpatented) and Columbia (unpatented), with neither of which it is directly related, but differs from them principally as follows:

1. Our variety grows taller than either Corona or Columbia.

2. Our variety is a faster propagator than either Columbia or Corona.

3. Our variety is more disease-resistant than either Corona or Columbia when grown under similar circumstances, and does not suffer from yellowing of the foliage like Corona.

4. Our variety has a longer flowerhead than Corona and a longer stem under the flowerhead than Columbia.

5. Spikes of our variety have stems that are more wiry than those of Corona, and a slimmer, stretchier tip.

6. Flowers of our variety have a predominantly white undertone instead of the creamy undertone of both Corona and Columbia.

7. The corona, halo, or picoteeing at the edge of the flowers of our variety is only about one-half as intense in color as that of Columbia when they are grown side by side.

8. Our variety has a waxy petal texture compared to the suede-like texture of Corona.

9. The flowers of our variety have less ruffling than those of Columbia, but more ruffling than those of Corona.

10. Our variety has heavier petal substance than either Columbia or Corona.

11. Our variety has healthier bulbs than either Columbia or Corona.

Having thus disclosed our invention, we claim:

The new and distinct variety of gladiolus plant substantially as herein shown and described, characterized particularly by its vigorous growth; its fast propagation; its apparent freedom from disease; its tall, wiry, and slender spikes; its regular placement of large flowers on the spikes, with all facing in one direction; the waxy texture and heavy substance of its flower petals; and the distinctive delicate rose, white and cream coloring as indicated.

No references cited.